(12) United States Patent
Tsao et al.

(10) Patent No.: US 8,833,939 B2
(45) Date of Patent: Sep. 16, 2014

(54) FUNDUS IMAGE DETECTION APPARATUS AND METHOD FOR OBTAINING FUNDUS IMAGE OF EYE OF ANIMAL

(71) Applicant: Altek Corporation, Hsinchu (TW)

(72) Inventors: Te-Chao Tsao, Hsinchu County (TW); Jui-Yuan Yu, Miaoli County (TW)

(73) Assignee: Altek Corporation, Hsinchu (TW)

( * ) Notice: Subject to any disclaimer, the term of this patent is extended or adjusted under 35 U.S.C. 154(b) by 0 days.

(21) Appl. No.: 13/736,071

(22) Filed: Jan. 8, 2013

(65) Prior Publication Data

US 2014/0192319 A1    Jul. 10, 2014

(51) Int. Cl.
*A61B 3/12* (2006.01)
*A61B 3/14* (2006.01)

(52) U.S. Cl.
CPC .... *A61B 3/12* (2013.01); *A61B 3/14* (2013.01)
USPC .......................................... 351/206; 351/205

(58) Field of Classification Search
CPC ........ A61B 3/0008; A61B 3/14; A61B 3/145; A61B 3/10; A61B 3/12; A61B 3/1208; A61B 5/14555; G06K 9/6255
USPC ...................................... 351/200, 206; 348/78
See application file for complete search history.

(56) References Cited

U.S. PATENT DOCUMENTS

| 5,615,278 | A | 3/1997 | Matsumoto | |
|---|---|---|---|---|
| 6,588,900 | B1 * | 7/2003 | Le Gargasson et al. | 351/200 |
| 2010/0061601 | A1 * | 3/2010 | Abramoff et al. | 382/117 |
| 2012/0224142 | A1 * | 9/2012 | Cornsweet et al. | 351/206 |
| 2012/0229617 | A1 * | 9/2012 | Yates et al. | 348/78 |
| 2013/0083184 | A1 * | 4/2013 | Yogesan et al. | 348/78 |

FOREIGN PATENT DOCUMENTS

TW          201019715         5/2010

* cited by examiner

*Primary Examiner* — Ricky Mack
*Assistant Examiner* — William Alexander
(74) *Attorney, Agent, or Firm* — Jianq Chyun IP Office

(57) ABSTRACT

A fundus image detection apparatus capable of detecting a fundus image of an eye of an animal is provided. The fundus image detection apparatus includes an image capturing unit and an image processing unit electrically connected with the image capturing unit. The image processing unit has a lookup table. The image processing unit corrects the fundus image of the eye of the animal according to the lookup table to diminish pincushion distortion. Moreover, a method for obtaining a fundus image of an eye of an animal is also provided.

12 Claims, 2 Drawing Sheets

FUNDUS IMAGE DETECTION APPARATUS AND METHOD FOR OBTAINING FUNDUS IMAGE OF EYE OF ANIMAL

BACKGROUND OF THE INVENTION

1. Field of the Invention

The invention generally relates to an optical apparatus, and more particularly, to a fundus image detection apparatus.

2. Description of Related Art

Eyes are the window to the soul, and the health of eyes is crucial to each one of us. Existing eye inspection apparatuses include pneuma-tonometers, refractometers, and fundus cameras. A fundus camera is an image detection apparatus used for inspecting the fundus of an eye, and which is used for detecting any degeneration on the fundus tissue, such as retina detachment. Besides, because blood vessels can be observed by looking at the fundus, fundus inspection can help to diagnose eye diseases. Especially, retina detachment (for example, retinal degeneration caused by diabetes) can be tracked through regular fundus inspections.

Because the fundus of an eye forms a cambered concave, the fundus image obtained by a fundus image detection apparatus comes with pincushion distortion. The pincushion distortion may cumber the doctor's diagnosis regarding the degeneration of the fundus tissue. To diminish the pincushion distortion on a fundus image, a conventional fundus image detection apparatus is usually disposed with special aspherical lenses. However, these aspherical lenses are very costly therefore are not suitable for low-cost handheld fundus image detection apparatuses.

SUMMARY OF THE INVENTION

Accordingly, the invention is directed to a fundus image detection apparatus capable of obtaining a high-quality fundus image of an eye of an animal.

An embodiment of the invention provides a fundus image detection apparatus adapted to detecting a fundus image of an eye of an animal. The fundus image detection apparatus includes an image capturing unit and an image processing unit. The depth of field of the image capturing unit is greater than or equal to 0.17 millimeter (mm). The image processing unit is electrically connected with the image capturing unit and is adapted to correcting the fundus image of the eye of the animal captured by the image capturing unit to diminish pincushion distortion.

An embodiment of the invention provides a fundus image detection apparatus adapted to detecting a fundus image of an eye of an animal. The fundus image detection apparatus includes an image capturing unit and an image processing unit. The image processing unit is electrically connected with the image capturing unit and has a lookup table. The image processing unit corrects the fundus image of the eye of the animal according to the lookup table to diminish pincushion distortion.

An embodiment of the invention provides a fundus image detection apparatus adapted to detecting a fundus image of an eye of an animal. The fundus image detection apparatus includes an image capturing unit and an image processing unit. The image capturing unit includes an image capturing element and a lens connected with the image capturing element. All lenses in the lens are spherical lenses. The image processing unit is electrically connected with the image capturing unit and is adapted to correcting the fundus image of the eye of the animal captured by the image capturing unit to diminish pincushion distortion.

An embodiment of the invention provides a method for obtaining a fundus image of an eye of an animal. The method includes following steps. The fundus image of the eye of the animal is captured. The fundus image of the eye of the animal is corrected to diminish pincushion distortion of the fundus image forming cambered concave.

According to an embodiment of the invention, the image processing unit has a lookup table. The image processing unit corrects the fundus image of the eye of the animal according to the lookup table to diminish pincushion distortion.

According to an embodiment of the invention, the image capturing unit captures a pincushion distortion pattern. The image processing unit has a built-in standard pattern data. The lookup table is generated by comparing the pincushion distortion pattern with the standard pattern data.

According to an embodiment of the invention, the image capturing unit includes an image capturing element, a lens cover, and a lens disposed between the lens cover and the image capturing element. The lens cover has the pincushion distortion pattern.

According to an embodiment of the invention, the image capturing unit further includes a light-emitting element. The light-emitting element is adapted to emit a light beam. The pincushion distortion pattern of the lens cover is disposed in the transmission path of the light beam.

According to an embodiment of the invention, the image capturing unit includes an image capturing element and a lens connected with the image capturing element. All lenses in the lens are spherical lenses.

According to an embodiment of the invention, the fundus image detection apparatus further includes an image storage unit. The image storage unit is electrically connected with the image processing unit and is adapted to storing the corrected fundus image of the eye of the image.

According to an embodiment of the invention, the step of correcting the fundus image of the eye of the animal to diminish pincushion distortion includes correcting the fundus image of the eye of the animal according to the lookup table to diminish pincushion distortion.

According to an embodiment of the invention, the method for obtaining the fundus image of the eye of the animal further includes following steps. A distorted pattern is captured. A standard pattern data is provided, where the lookup table is generated by comparing the distorted pattern with the standard pattern data.

According to an embodiment of the invention, the method for obtaining the fundus image of the eye of the animal further includes following step after the step of correcting the fundus image of the eye of the animal to diminish pincushion distortion. The corrected fundus image of the eye of the animal is stored.

As described above, embodiments of the invention provide a fundus image detection apparatus and a method for obtaining a fundus image of an eye of an animal, in which the fundus image of the eye of the animal is corrected to diminish pincushion distortion. Thereby, the fundus image detection apparatus and the method for obtaining a fundus image of an eye of an animal provided by embodiments of the invention can provide a high-quality fundus image of the animal eye.

These and other exemplary embodiments, features, aspects, and advantages of the invention will be described and become more apparent from the detailed description of exemplary embodiments when read in conjunction with accompanying drawings.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
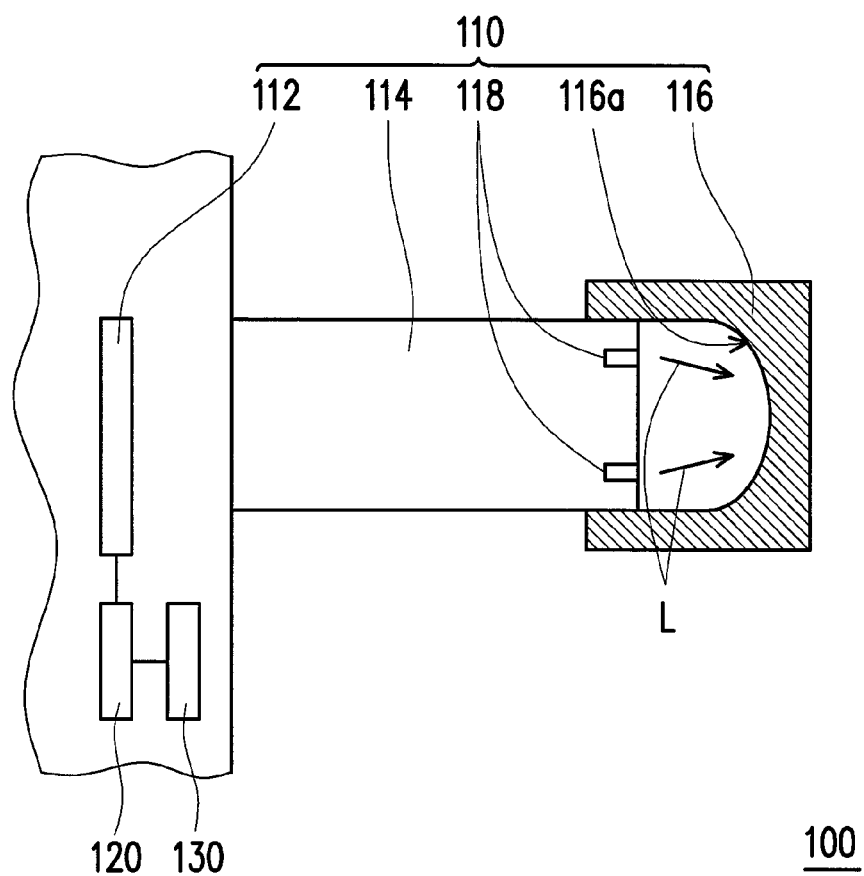
FIG. 1 is a diagram of a fundus image detection apparatus according to an embodiment of the invention.

Reference will now be made in detail to the present preferred embodiments of the invention, examples of which are illustrated in the accompanying drawings. Wherever possible, the same reference numbers are used in the drawings and the description to refer to the same or like parts.
Fundus Image Detection Apparatus FIG. 1 is a diagram of a fundus image detection apparatus according to an embodiment of the invention. Referring to FIG. 1, the fundus image detection apparatus 100 is adapted to detecting a fundus image of an eye of an animal. In the present embodiment, the fundus image detection apparatus 100 can be used for detecting fundus images of human eyes. However, the invention is not limited thereto, and in other embodiments, the fundus image detection apparatus 100 can also be used for detecting fundus images of eyes of other animals, such as dogs, cats, cattle, sheep, horses, and pigs. Additionally, the eyes of animals may be eyes with cambered fundus.

In the present embodiment, the fundus image detection apparatus 100 includes an image capturing unit 110 and an image processing unit 120 electrically connected with the image capturing unit 110. The image capturing unit 110 is configured to capture fundus images of eyes of animals. The image processing unit 120 is configured to correct the fundus images of animal eyes captured by the image capturing unit 110 to diminish pincushion distortion. In the present embodiment, the image capturing unit 110 can capture dynamic or static fundus images of animals' eyes, and whether the image capturing unit 110 captures dynamic or static fundus images is determined according to the user's requirement.

In an embodiment of the invention, the image capturing unit 110 includes an image capturing element 112 (for example, a charge-coupled device) and a lens 114 connected with the image capturing element 112. It should be mentioned that in the present embodiment, the fundus image detection apparatus 100 corrects fundus images of animal eyes to diminish pincushion distortion by using the image processing unit 120. To be specific, the fundus image detection apparatus 100 may correct fundus images to diminish pincushion distortion by using a firmware, a software, or a digital logic circuit. Thus, it is not necessary to implement lenses in the lens 114 with distortion-correcting but high-cost aspherical lenses. In the present embodiment, all the lenses in the lens 114 are spherical lenses. Accordingly, the cost of the fundus image detection apparatus 100 is reduced.

In another embodiment of the invention, the image processing unit 120 has a built-in lookup table. The image processing unit 120 corrects fundus images of animal eyes to diminish pincushion distortion according to the lookup table. In other words, in the present embodiment, the pincushion distortion diminishing correction can be carried out through table lookup (i.e., by using the lookup table) instead of the real-time operation in the conventional technique, so that the performance of the fundus image detection apparatus in obtaining high-quality fundus images of animal eyes can be improved. Accordingly, when a user is about to obtain live-view fundus images of an eye of an animal, the fundus image detection apparatus 100 can provide live-view images to the user with its high image processing performance, so that the user can determine the image capturing range accordingly.

Figure 2:
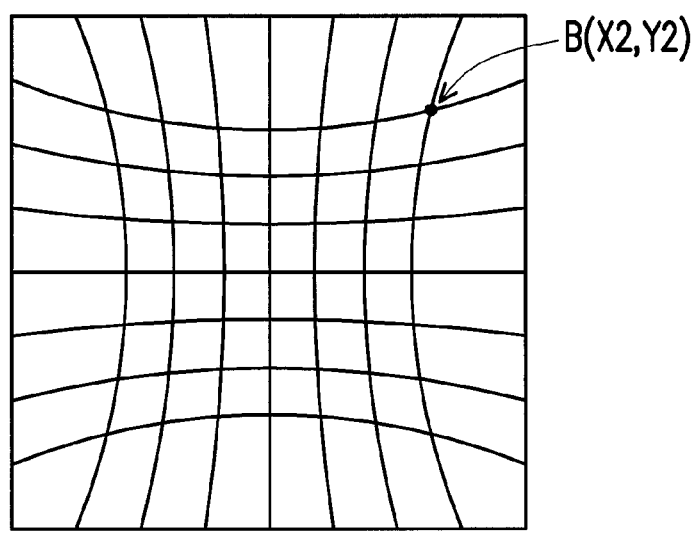
FIG. 2 is a diagram of a pincushion distortion pattern according to an embodiment of the invention.
Figure 3:
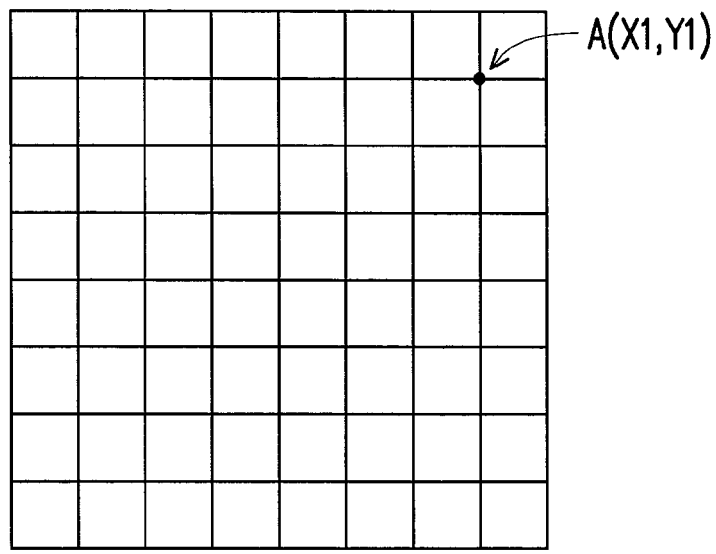
FIG. 3 is a diagram of a standard pattern data according to an embodiment of the invention.

In the present embodiment, the correction data for diminishing pincushion distortion is first calculated by using an external computer software, and the correction data is stored as aforementioned lookup table. Then, the lookup table is built in the image processing unit 120 so that the image processing unit 120 can perform the pincushion distortion diminishing correction accordingly. However, in the invention, the generation of the lookup table is not limited to the technique described above. For example, in other embodiments, the image capturing unit 110 may capture a pincushion distortion pattern, and the image processing unit 120 may have a built-in standard pattern data (i.e., pattern data without any distortion). FIG. 2 is a diagram of a pincushion distortion pattern according to an embodiment of the invention. FIG. 3 is a diagram of a standard pattern data according to an embodiment of the invention. Referring to FIG. 2 and FIG. 3, the lookup table is generated by comparing the standard pattern data 200 with the pincushion distortion pattern 300 (for example, by calculating the offset data of each pixel in the pincushion distortion pattern after the pixel is corrected). To be specific, the standard pattern data 200 and the pincushion distortion pattern 300 respectively have corresponding dot A and dot B. The dot A has coordinates (X1,Y1), and the dot B has coordinates (X2,Y2). The coordinate difference (ΔX,ΔY) is obtained by comparing the coordinates (X2,Y2) of dot B with the coordinates (X1,Y1) of dot A. Herein ΔX=X2−X1, and ΔY=Y2−Y1. By using this coordinate difference (ΔX, ΔY), the pixel in the fundus image captured by the image capturing unit 110 corresponding to the dot B can be corrected to an appropriate position, so that pincushion distortion in the fundus image is diminished.

Additionally, during the process of correcting pixel positions by using aforementioned coordinate differences, some pixels in the fundus image may not have any corresponding dot in the pincushion distortion pattern 300. In this case, an interpolation operation can be carried out by using a bilinear algorithm and another pixel which is adjacent to the current pixel and has a corresponding dot in the pincushion distortion pattern 300, so that pixels in the fundus image which have no corresponding dot in the pincushion distortion pattern 300 can still be corrected to appropriate positions. Thereby, the fundus image detection apparatus 100 can obtain a fundus image of an animal eye with low pincushion distortion.

Referring to FIG. 1 again, to be specific, in an embodiment of the invention, the image capturing unit 110 selectively includes a lens cover 116. The lens 114 is disposed between the lens cover 116 and the image capturing element 112, and a distorted pattern is disposed on a surface 116a of the lens cover 116 that is facing the lens 114. The surface 116a may be a cambered concave. The image capturing unit 110 further includes a light-emitting element 118. In the present embodiment, the light-emitting element 118 may be a light emitting diode (LED). However, the invention is not limited thereto. The light-emitting element 118 is configured to emit a light beam L. The pincushion distortion pattern of the lens cover 116 is disposed in the transmission path of the light beam L. Before the fundus image detection apparatus 100 detects a fundus image of an animal eye, the light-emitting element 118 emits the light beam L to the distorted pattern of the lens cover 116, so that the image capturing unit 110 can capture the distorted pattern (for example, the distorted pattern 300 illustrated in FIG. 2). To be specific, the distorted pattern on the lens cover 116 may be equally spaced lines that perpendicularly intersect each other on a cambered surface (i.e., the surface 116a). Even though these perpendicularly crossed lines are equally spaced on the cambered surface, because the sensing surface of the image capturing element 112 is a flat surface, pincushion distortion (as shown in FIG. 2) will be produced on the image captured by the image capturing element 112. Thereafter, the image processing unit 120 obtains a lookup table by comparing the distorted pattern 300 with the built-in standard pattern data 200 and corrects fundus images subsequently captured by the image capturing unit 110 to diminish pincushion distortion according to the lookup table.

In the present embodiment, the fundus image detection apparatus 100 further includes an image storage unit 130. The image storage unit 130 is electrically connected with the image processing unit 120 and is configured to store fundus images on which the pincushion distortion diminishing correction has been performed. In other words, in the present embodiment, the fundus image detection apparatus 100 performs the pincushion distortion diminishing correction before storing a fundus image. Thus, the fundus image to be corrected to diminish pincushion distortion does not undergo compression or any other image processing, so that the image processing unit 120 can perform the pincushion distortion diminishing correction on the most original fundus image and obtain a high-quality image with low pincushion distortion.

In yet another embodiment of the invention, the depth of field of the image capturing unit 110 is greater than or equal to 0.17 millimeter (mm). Through the appropriate design of the depth of field, the fundus image detection apparatus 100 is more adapted to detecting fundus images of animal eyes and providing high-quality images.

Method for Obtaining a Fundus Image of an Eye of an Animal

Figure 4:
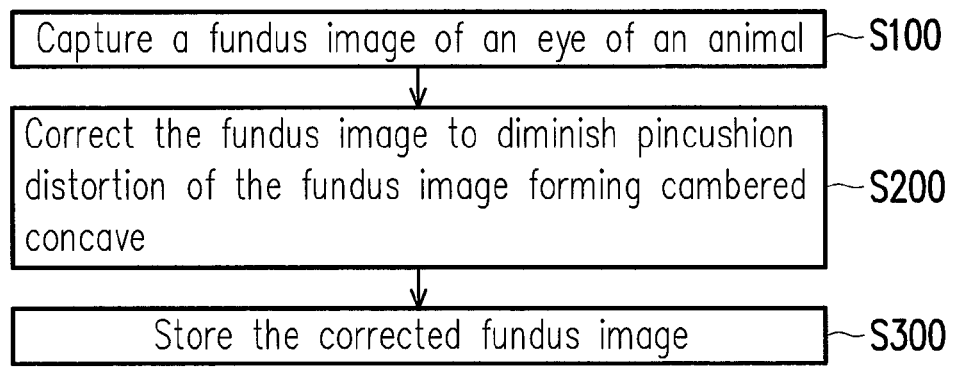
FIG. 4 is a flowchart of a method for obtaining a fundus image of an eye of an animal according to an embodiment of the invention.

FIG. 4 is a flowchart of a method for obtaining a fundus image of an eye of an animal according to an embodiment of the invention. Referring to FIG. 4, first, a fundus image of an eye of an animal is captured (step S100). Then, the fundus image is corrected to diminish pincushion distortion of the fundus image forming cambered concave (step S200).

In the present embodiment, the fundus image is corrected to diminish pincushion distortion according to the lookup table. In other words, in the present embodiment, the conventional technique in which the pincushion distortion diminishing correction is performed through real-time operation is abandoned. Instead, the pincushion distortion is diminished through table lookup (i.e., according to the lookup table), so that the speed of obtaining fundus images with low pincushion distortion is improved. In addition, the positions of some distorted pixels can be re-arranged, and empty pixel positions can be filled up through interpolation. In the present embodiment, the lookup table is established in advance through an external computer software. However, in the invention, the technique of generating the lookup table is not limited to that mentioned above. For example, in other embodiments, a pincushion distortion pattern is captured, and a standard pattern data is provided. Then, the pincushion distortion pattern is compared with the standard pattern data to obtain the lookup table. The technique for generating a lookup table has been explained in detail in foregoing section of the "fundus image detection apparatus" therefore will not be described herein.

Referring to FIG. 4 again, in the method for obtaining a fundus image of an eye of an animal provided by the present embodiment, after a fundus image is corrected to diminish pincushion distortion, the corrected fundus image is stored (step S300). In other words, in the present embodiment, the pincushion distortion diminishing correction is performed before the fundus image is stored. Thus, the fundus image to be corrected to diminish pincushion distortion does not undergo compression or any other image processing and is the most original data (Raw Data). Thus, the method for obtaining fundus images of animal eyes provided by the present embodiment can perform a precise pincushion distortion correction and obtain a high-quality fundus image of an animal eye.

As described above, in a fundus image detection apparatus and a method for obtaining a fundus image of an eye of an animal provided by an embodiment of the invention, the fundus image of the eye of the animal is corrected to diminish pincushion distortion. Thereby, the fundus image detection apparatus and the method for obtaining a fundus image of an eye of an animal provided by the embodiment of the invention can provide a high-quality fundus image of the animal eye.

In a fundus image detection apparatus provided by another embodiment of the invention, the pincushion distortion diminishing correction is performed on a fungus image by using a firmware, a software, or a digital logic circuit. Thus, no high-cost aspherical lens is disposed in the fundus image detection apparatus for diminishing pincushion distortion, so that the cost of the fundus image detection apparatus is reduced.

In a fundus image detection apparatus and a method for obtaining a fundus image of an eye of an animal provided by yet another embodiment of the invention, the conventional real-time operation is replaced by lookup table to diminish pincushion distortion, so that high-quality fundus image can be quickly obtained.

In a fundus image detection apparatus provided by still another embodiment of the invention, through appropriate design of the depth of field of the image capturing unit, the fundus image detection apparatus is more adapted to detecting fungus images of animal eyes and obtaining high-quality images.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A fundus image detection apparatus, adapted to detecting a fundus image of an eye of an animal, the fundus image detection apparatus comprising:
   an image capturing unit, wherein a depth of field of the image capturing unit is greater than or equal to 0.17 millimeter (mm); and
   an image processing unit, electrically connected with the image capturing unit, and adapted to correcting the fundus image of the eye of the animal captured by the image capturing unit to diminish pincushion distortion, wherein the image processing unit has a lookup table, the image capturing unit captures a pincushion distortion pattern, the image processing unit has a built-in standard pattern data, and the lookup table is generated by comparing the pincushion distortion pattern with the standard pattern data, and the image processing unit corrects the fundus image of the eye of the animal to diminish pincushion distortion according to the lookup table.

2. The fundus image detection apparatus according to claim 1, wherein the image capturing unit comprises an image capturing element, a lens cover, and a lens disposed between the lens cover and the image capturing element, and the lens cover has the pincushion distortion pattern.

3. The fundus image detection apparatus according to claim 2, wherein the image capturing unit further comprises a light-emitting element adapted to emitting a light beam, and the pincushion distortion pattern of the lens cover is disposed in a transmission path of the light beam.

4. The fundus image detection apparatus according to claim 1, wherein the image capturing unit comprises an image capturing element and a lens connected with the image capturing element, wherein all lenses in the lens are spherical lenses.

5. The fundus image detection apparatus according to claim 1 further comprising an image storage unit electrically connected with the image processing unit, wherein the image storage unit is adapted to storing the corrected fundus image of the eye of the animal.

6. A fundus image detection apparatus, adapted to detecting a fundus image of an eye of an animal, the fundus image detection apparatus comprising:
　an image capturing unit; and
　an image processing unit, electrically connected with the image capturing unit and having a lookup table, wherein the image capturing unit captures a pincushion distortion pattern, the image processing unit has a built-in standard pattern data, and the lookup table is generated by comparing the pincushion distortion pattern with the standard pattern data, and the image processing unit corrects the fundus image of the eye of the animal to diminish pincushion distortion according to the lookup table.

7. The fundus image detection apparatus according to claim 6, wherein the image capturing unit comprises an image capturing element, a lens cover, and a lens disposed between the lens cover and the image capturing element, and the lens cover has the pincushion distortion pattern.

8. The fundus image detection apparatus according to claim 7, wherein the image capturing unit further comprises a light-emitting element adapted to emitting a light beam, and the pincushion distortion pattern of the lens cover is disposed in a transmission path of the light beam.

9. The fundus image detection apparatus according to claim 6, wherein the image capturing unit comprises an image capturing element and a lens connected with the image capturing element, wherein all lenses in the lens are spherical lenses.

10. The fundus image detection apparatus according to claim 6 further comprising an image storage unit electrically connected with the image processing unit, wherein the image storage unit is adapted to storing the corrected fundus image of the eye of the animal.

11. A method for obtaining a fundus image of an eye of an animal, comprising:
　capturing the fundus image of the eye of the animal; and
　correcting the fundus image of the eye of the animal to diminish pincushion distortion of the fundus image forming cambered concave, wherein the step of correcting the fundus image of the eye of the animal to diminish pincushion distortion comprises:
　capturing a distorted pattern;
　providing a standard pattern data;
　comparing the distorted pattern with the standard pattern data to generate a lookup table; and
　correcting the fundus image of the eye of the animal to diminish pincushion distortion according to the lookup table.

12. The method according to claim 11, wherein after correcting the fundus image of the eye of the animal to diminish pincushion distortion, the method further comprises storing the corrected fundus image of the eye of the animal.

* * * * *